United States Patent
Burris et al.

[19]

[11] Patent Number: 5,924,988
[45] Date of Patent: Jul. 20, 1999

[54] ULTRASOUND SYSTEM DISPLAY DEVICE

[75] Inventors: David E. Burris, Santa Cruz; Richard W. Henderson, Fremont; John R. Dovala, San Jose; Thomas J. Markiewicz, Los Gatos; Anastasia M. Mikula-Curtis, Saratoga; Joseph J. Molinari, Redwood City, all of Calif.

[73] Assignee: Acuson Corporation, Mountain View, Calif.

[21] Appl. No.: 08/834,653

[22] Filed: Apr. 11, 1997

[51] Int. Cl.[6] ........................................................ A61B 8/00
[52] U.S. Cl. .............................................................. 600/437
[58] Field of Search ..................................... 600/437, 441, 600/443, 447, 903

[56] References Cited

U.S. PATENT DOCUMENTS

| | | | |
|---|---|---|---|
| 4,625,731 | 12/1986 | Quedens et al. | 600/443 |
| 5,129,397 | 7/1992 | Jingu et al. | 600/437 |
| 5,268,817 | 12/1993 | Miyagawa et al. | 361/729 |
| 5,457,831 | 10/1995 | Foster et al. | 5/510 |
| 5,549,004 | 8/1996 | Nugent | 73/622 |
| 5,590,658 | 1/1997 | Chiang et al. . | |
| 5,687,717 | 11/1997 | Halpern et al. | 128/903 |
| 5,690,114 | 11/1997 | Chiang et al. | 600/447 |
| 5,722,411 | 3/1998 | Suzuki et al. . | |
| 5,722,412 | 3/1998 | Pflugrath et al. . | |
| 5,738,099 | 4/1998 | Chong | 600/437 |

OTHER PUBLICATIONS

Dow Jones News Report "Advanced Technology Laboratories Inc. (ATLI) and the University of Washington plan a $12.6–million project to develop an ultrasound diagnostic instrument." Dow Jones News Feb. 28, 1996, Dow Jones & Co., Inc.

Abstract for "Portable Ultrasound Device For Battlefield Trauma" presented at DARPA/ONR Workshop on Medical Ultrasonic Imaging Technology Development for Combat Casualty Care at Lansdowne Conference Center, Lansdowne, Virginia on Feb. 12–14, 1997.

*Primary Examiner*—Francis J. Jaworski
*Attorney, Agent, or Firm*—Brinks Hofer Gilson & Lione

[57] ABSTRACT

A diagnostic medical imaging ultrasound system comprises a flat panel display device to provide ultrasound images to an operator. The flat panel display device produces an image with sufficient contrast ratio, response time, and angular fidelity to display high-quality ultrasound images. The display device is secured to an ultrasound system cart and can be positioned away from the cart. The display device can also be secured to a structure that is physically independent from an ultrasound image generator and can be ergonomically positioned with respect to a patient and operator for superior ergonomics.

29 Claims, 9 Drawing Sheets

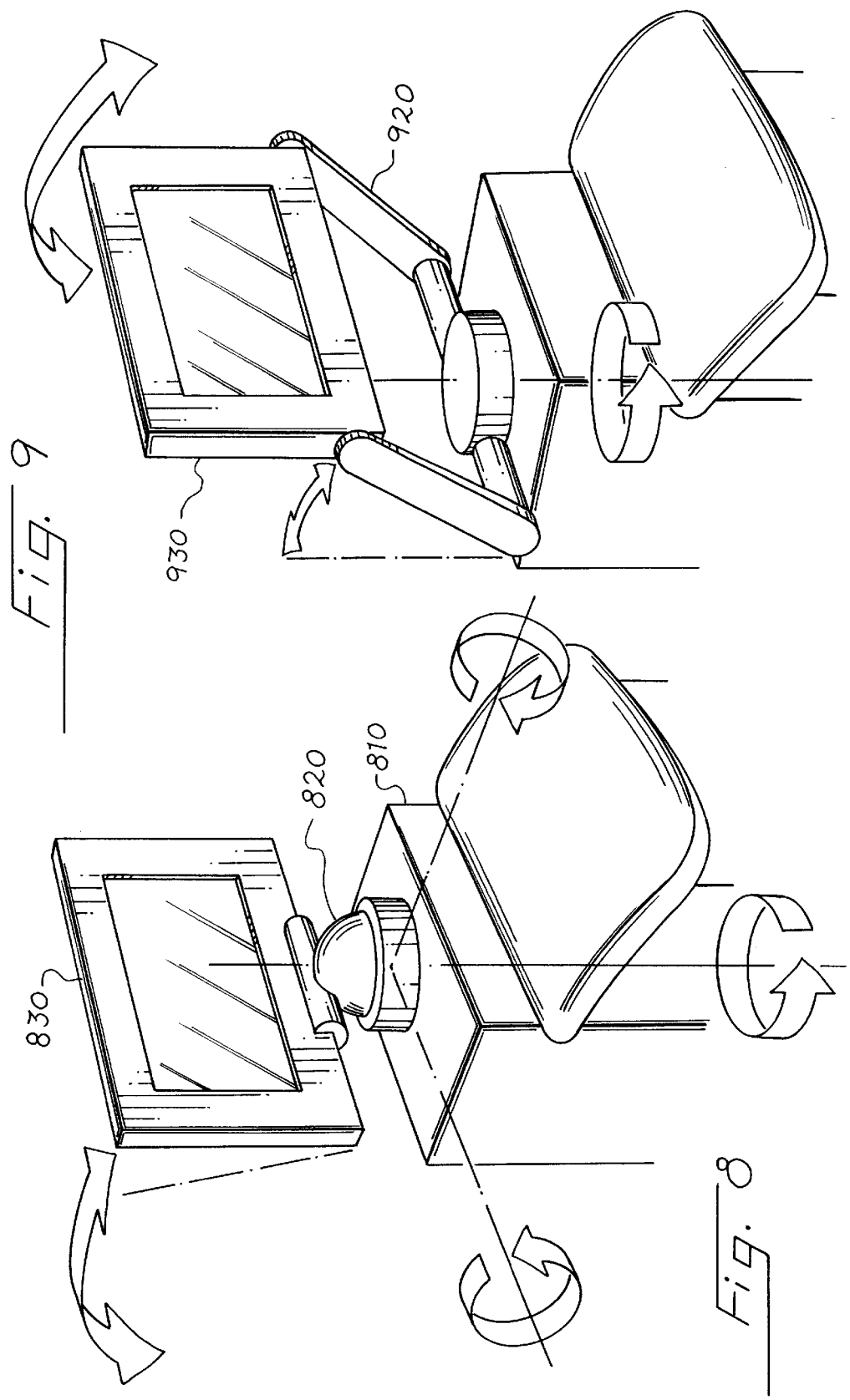

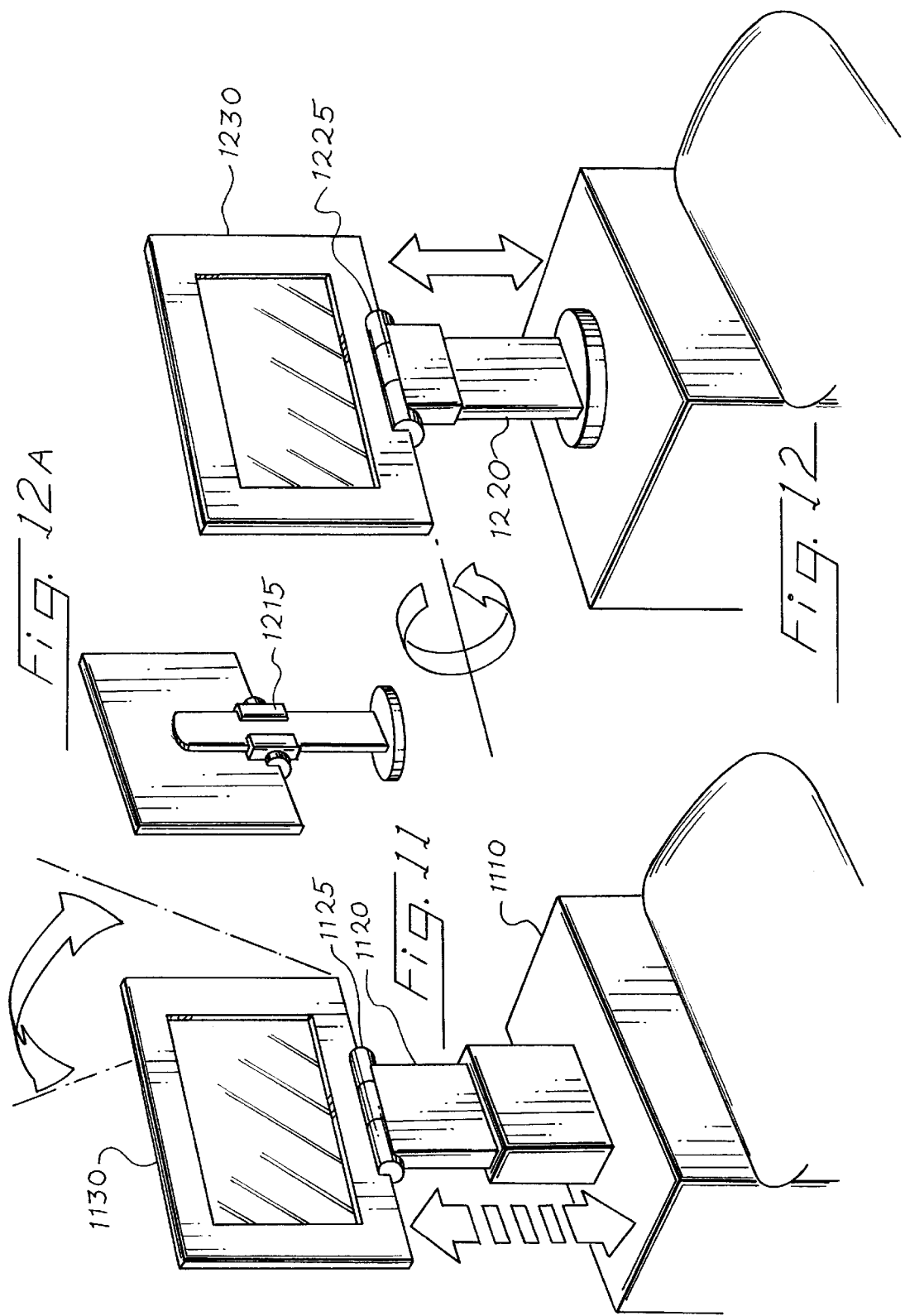

ULTRASOUND SYSTEM DISPLAY DEVICE

BACKGROUND OF THE INVENTION

In a typical ultrasound examination, an ultrasound operator interfaces with four primary elements: a patient, a transducer which sends and receives ultrasound signals, an ultrasound generator, and a display device for presenting ultrasound images and interface messages. With typical ultrasound systems, the display device has very limited positioning in relation to the size and weight of the ultrasound generator, and, as a result, operator ergonomics are compromised.

The most common ultrasound system uses an ultrasound system cart to carry the ultrasound generator and a cathode ray tube (CRT) display device, which rests on top of the cart (usually at the operator's eye level), to present generated ultrasound images. To use this system to perform an ultrasound examination, the operator positions the cart near the patient. Because of patient positioning and the physical layout of the examination room, the CRT display and cart are not optimally positioned for preferred operator ergonomics for performing the ultrasound examination. Accordingly, the operator must frequently turn his head from the patient to the CRT display during the course of the examination. This may cause body strain, increased operator fatigue, and loss of efficiency.

The size and weight of the CRT display device raise the center of gravity of the cart. To ensure stability in static and dynamic conditions, the cart must exhibit certain structure requirements to respond to the high center of gravity, resulting in larger cart sizes to ensure acceptable stability limits. Even as ultrasound generators become smaller, a large cart footprint is typically implemented to meet stability requirements. This prohibits a highly compact, portable ultrasound system.

Another ultrasound imaging system is disclosed in U.S. Pat. No. 5,590,658. In this system, a lap-top computer with a flat panel display is used for data processing and display of ultrasound images gathered by a coupled scan head. As suggested by FIG. 3 of this patent, the display has some rotation about a horizontal axis, but it does not appear to be capable of movements greater than 90 degrees from a vertical axis.

In an ultrasound system proposed by Advanced Technology Laboratories, Inc. entitled "Portable Ultrasound Device for Battlefield Trauma," a hand-held device performs transmit/receive beamforming, digital signal processing, and image generation on a flat panel display. This proposed system uses a common housing for the display and generator.

There is, therefore, a need for an ultrasound system that provides increased ease of use.

SUMMARY OF THE INVENTION

The present invention is directed to an ultrasound system display device, which provides a high-quality display image and allows an operator to separately position the display device from an ultrasound generator.

According to a first aspect of this invention, a flat panel display device is provided capable of producing an image with a sufficient contrast ratio, response time, and angular fidelity to adequately display ultrasound images.

According to a second aspect of this invention, a flat panel display device is supported by an ultrasound system cart, which carries an ultrasound image generator.

According to a third aspect of this invention, the flat panel display device is secured to an ultrasound system cart with means for multiple positioning of the display device with respect to the cart.

According to a fourth aspect of this invention, a flat panel display device is secured to a structure that is physically independent from the ultrasound system generator with means for positioning the display device with respect to a patient.

The preferred embodiments of the invention will now be described with reference to the attached drawings.

BRIEF DESCRIPTION OF THE DRAWINGS

FIG. 5 is a perspective view of a means for positioning a flat panel display device using a hinge and an arm.

FIG. 8 is a perspective view of a means for positioning a flat panel display device using a ball and socket to provide the display device with freedom to position in multiple axes.

FIG. 9 is a perspective view of a means for positioning a flat panel display device using a swiveling yoke to tilt, swivel, and adjust a fore-and-aft position of the display device.

FIG. 11 is a perspective view of a means for positioning a flat panel display device using a hinge and telescopic slide to tilt and adjust a vertical position of the display device.

FIG. 12 is a perspective view of a means for positioning a flat panel display device using a hinge, sleeve, and vertical slide to adjust a vertical position of and to tilt the display device.

FIG. 12A is a rear view of the means shown in FIG. 12.

DETAILED DESCRIPTION OF THE PRESENTLY PREFERRED EMBODIMENTS

FIRST PREFERRED EMBODIMENT

Figure 1:
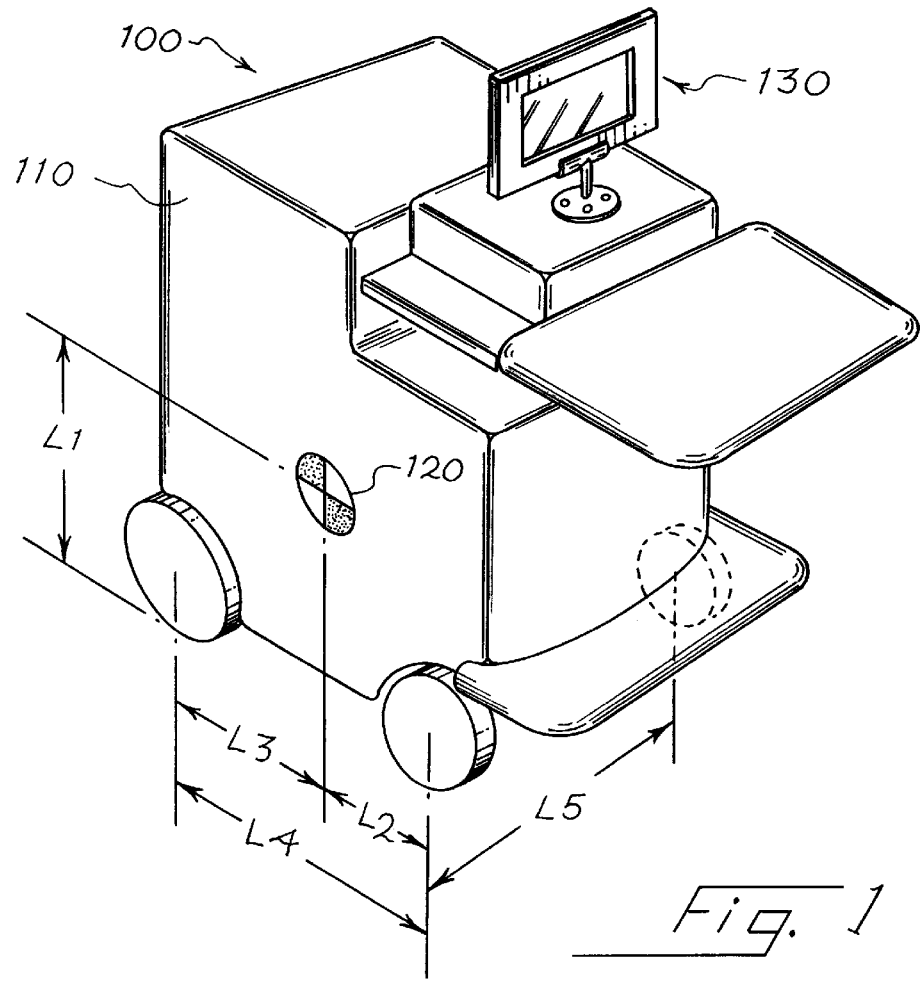
FIG. 1 is a perspective view of a diagnostic medical imaging ultrasound system of a first preferred embodiment.

Turning now to the drawings, FIGS. 1 shows a diagnostic medical imaging ultrasound system 100 of a first preferred embodiment. In this system 100, an ultrasound system cart 110, with a center of gravity 120, carries an ultrasound image generator 200 (see FIG. 2) and supports a flat panel display device 130. Typically, an operator of this system 100 positions the cart 110 near a patient and performs ultrasound imaging using the ultrasound image generator 200 housed in the cart 110. The flat panel display device 130 presents the image to the operator. Each of the components of this ultrasound system 100 will be discussed below.

The Ultrasound Image Generator 200

Figure 2:
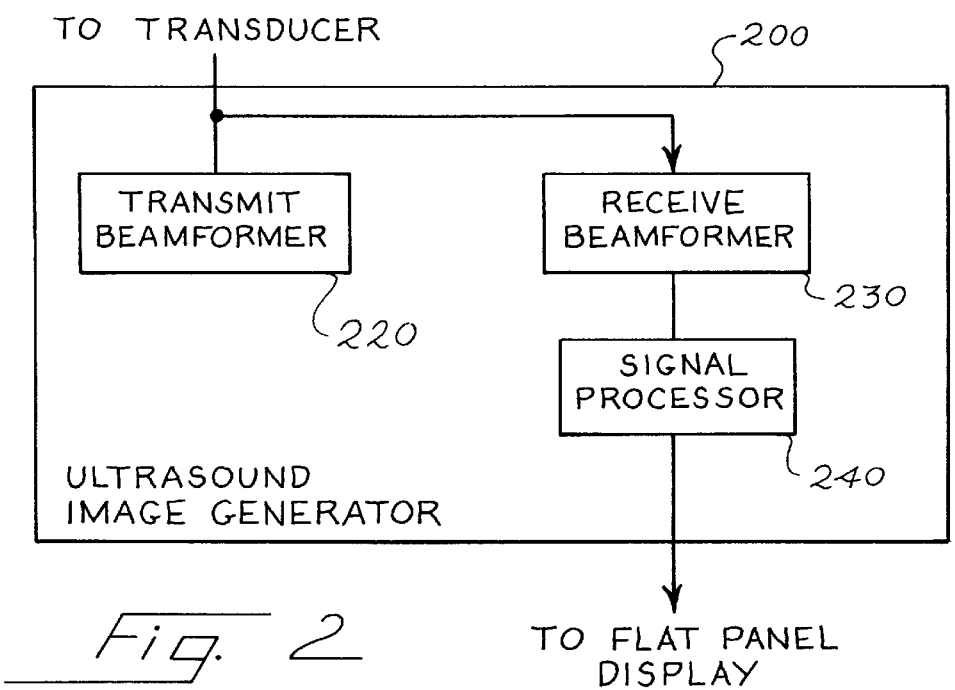
FIG. 2 is a block diagram of an ultrasound image generator used in the embodiment of FIG. 1.

FIG. 2 shows components that comprise the ultrasound image generator 200: a transmit beamformer 220, a receive beamformer 230, and a signal processor 240 responsive to the receive beamformer 230 and coupled to the flat panel display device 130.

These components function together to construct an ultrasound image of a patient. The transmit beamformer 220 sends ultrasonic energy to a particular portion of the patient's body via a transducer, and the receive beamformer 230 gathers the resulting reflected ultrasound wave. The signal processor 240 interprets the gathered reflected wave to generate the ultrasound image on the flat panel display device 130.

It is important to note that any type of ultrasound image generator currently available or developed in the future can be used with the embodiments described herein.

The Flat Panel Display Device 130

The flat panel display device 130 displays the generated ultrasound image to the operator. As used herein, the term "flat panel display device" is used to refer to the flat panel display itself along with a protective enclosure surrounding the display, if such an enclosure is used. The enclosure will be discussed in more detail below.

A flat panel display is any display having a depth significantly less than the diagonal length of its face. There are many technologies which may be used to construct a flat panel display. By way of example, such displays may include, but are not limited to, liquid crystal displays, field emissive displays, and plasma displays. The image-producing technology can be transmissive (such as active or passive matrix liquid crystal displays) or emissive (such as high or low voltage field emissive, electroluminescent, or plasma displays).

Each of these display technologies is more lightweight and smaller in volume as compared to existing CRT technologies, and most of them offer reduced power consumption. Accordingly, flat panel displays typically weigh less than about 10 lbs, are less than about 16 cm in depth, and require less than about 30 watts of power to operate.

Preferably, the flat panel display device 130 is a color display, which when considered as a functional assembly, is capable of emitting light, as well as having characteristics described below.

The image produced by the display preferably has a contrast ratio greater than about 300:1, preferably greater than about 1,000:1. As used herein, "contrast ratio" in a display that emits light is a quotient of (1) the peak luminance of the display and (2) the lowest luminance simultaneously reproducible by the display.

The image produced by the display preferably has a response time of about 33 msec or less. This allows for a faithful representation of motion in the image with a display refresh rate of about 30 Hz or more. "Response time" in a display capable of emitting light is the amount of time for a picture element to return from a fully excited condition to a state with $\frac{1}{10}$-th the luminance of the fully excited state.

The image produced by the display preferably also has angular fidelity within a ±45 degree cone originating from and comprising an axis of symmetry upright to the face of the flat panel display. As is well known is the art, "angular fidelity" refers to the following condition: the x and y coordinates of the 1931 Commission Internationale de l'Eclairage (CIE) 2-degree chromaticity diagram deviating less than ±0.030 from the x and y values measured upright to the display's face and the image contrast being within ±50% of the contrast value measured upright to the display's face. The 1931 CIE 2-degree chromaticity diagram, combined with the luminance value or contrast, is one of the most popular of the industry standards for specifying all three attributes of a color.

Additionally, the display preferably has an active image area larger than about 10 inch diagonal, and a total display color pixel count greater than about 400,000, preferably greater than about 750,000.

The flat panel display device is responsive to the ultrasound image generator 200. The display device 130 may require electrical connection to the ultrasound image generator 200 for power and display data. Depending on the electrical configuration of the ultrasound image generator 200 and the display device 130, the display device 130 can be added to an already existing generator 200 without significant changes to its input/output architecture.

If the display device has a power source independent of the generator 200, the display device 130 can be responsive to the ultrasound image generator 200 without any physical connection, such as a wire or cable, to the generator 200. That is, any suitable connection (including, but not limited to, an infrared link) can be used to transmit ultrasound data from the signal processor 240 to the display device 130.

Figure 3:
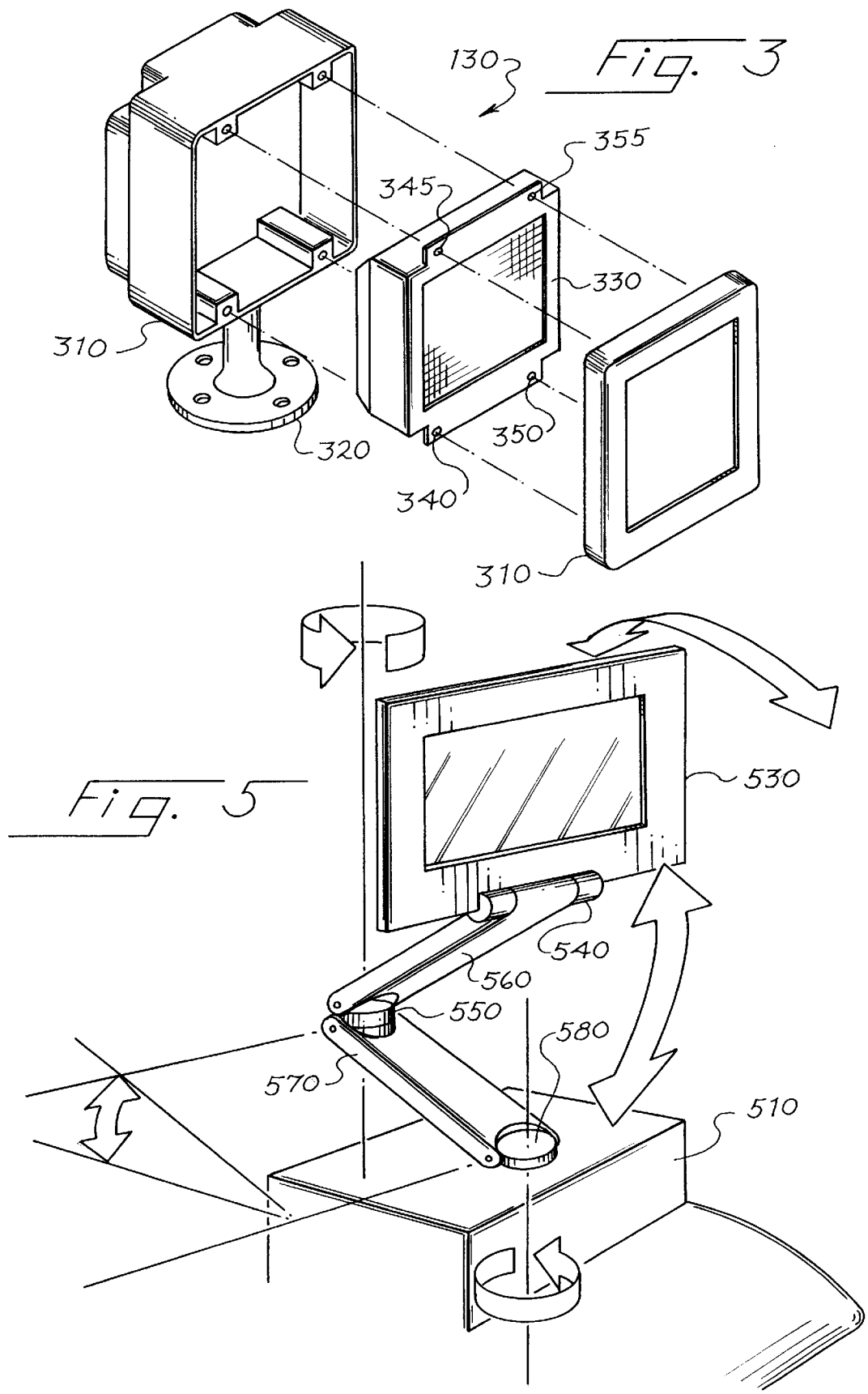
FIG. 3 is a perspective view of a protective enclosure for a flat panel display of the preferred embodiment of FIG. 1.

As mentioned above and shown in FIG. 3, a protective enclosure 310 can surround the flat panel display 330 to form the display device 130. The enclosure 310 of FIG. 3 is a two-piece clam-shell design that secures into attachment points 340, 345, 350, 355 on the flat panel display 330 with appropriate hardware, such as screws. It is important to note that other enclosure designs and other means for securing the enclosure to the flat panel display 330 can be used.

The enclosure 310 can also incorporate a mounting pad 320 to secure the flat panel display device 130 to the ultrasound system cart 110. For example, mechanical hardware, such as screws, can secure the mounting pad 320 into a base plate (not shown) included in the ultrasound system cart 110. Other means for securing the display device 130 can also be used.

The Ultrasound System Cart 110

The ultrasound system cart 110 carries the ultrasound image generator 200 and supports the flat panel display device 130. As will be discussed in more detail below, one advantage of using a flat panel display device is that its lightweight and compact design allows the ultrasound system cart 110 to have a lower center of gravity 120.

More specifically, as shown in FIG. 1, the cart 110 preferably has a center of gravity 120 less than about 24 inches from the floor (shown as distance L1) and less than about 14 inches from the front and rear wheel centerlines (shown as distances L2 and L3, respectively). The cart can also have a wheelbase length less than about 27 inches (shown as distance L4) and a track width less than about 22 inches (shown as distance L5).

Advantages

Using a flat panel display device as described above leads to advantages over the prior-art flat panel and CRT displays described above. Unlike the flat panel displays of the systems discussed in the Background section, the image produced by the flat panel display of these embodiments has a contrast ratio, response time, and angular fidelity to provide the operator with a high-quality display of the image information generated by the signal processor.

The contrast ratio enables an operator to reliably resolve tissue subtleties resulting from a broad range of clinical conditions. The fast response time is needed to accurately represent fast-moving tissues, which is essential for making accurate diagnoses in cardiovascular and pediatric exams. Angular fidelity of the display image allows an operator to maintain diagnostic precision (which involves the aforementioned image contrast, and also usage of color in certain ultrasound diagnostic modalities) over a typical range of head-to-display movement occurring during clinical ultrasound examinations.

The flat panel display described in this embodiment also has advantages over CRT displays now commonly used, in that the flat panel display requires less power to operate and is less prone to corner misconvergence, geometry distortion, and stray magnetic fields.

Additionally, the size and weight of the flat panel display allow for a smaller cart 110. As discussed above, by using a flat panel display, the ultrasound system cart 110 can have a lower center of gravity 120. Because of this, the footprint of the cart 110 can be reduced to provide a more portable ultrasound system without sacrificing static or dynamic stability, something not possible with a CRT display. Furthermore, a smaller cart size reduces the visual volume of the ultrasound system 100, making the system 100 less intimidating to the patient. Even if cart size is not reduced, using a smaller display device provides the cart 110 with more available storage space.

Finally, because the flat panel display device 130 is lightweight, it can be positioned away from the cart 110, as will be described in more detail below in connection with the second preferred embodiment.

SECOND PREFERRED EMBODIMENT

Figure 4:
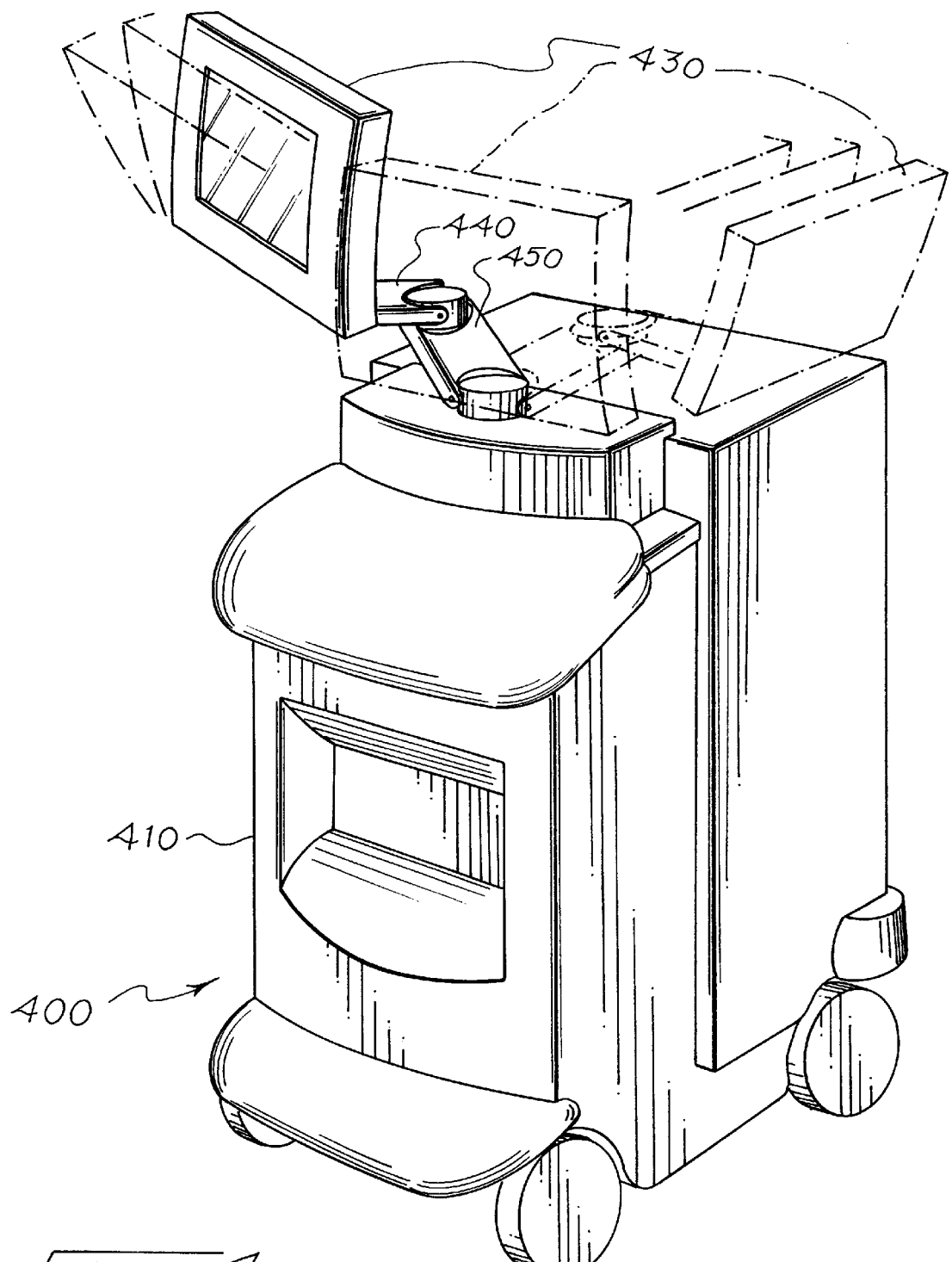
FIG. 4 is a perspective view of a diagnostic medical imaging ultrasound system of a second preferred embodiment.

FIG. 4 illustrates a diagnostic medical imaging ultrasound system 400 of a second preferred embodiment. As in the first preferred embodiment, an ultrasound system cart 410 carries an ultrasound image generator 200 of the type described above and supports a flat panel display device 430. The structure and function of each of these components is the same as those described in system 100 of the first preferred embodiment.

Instead of merely being supported by the ultrasound system cart as in the first preferred embodiment, the flat panel display device 430 of this system 400 attaches to a support apparatus comprising two swiveling arms 440, 450. One swiveling arm 440 connects to the flat panel display device 430 in a way that allows the operator to tilt the display device 430, as shown in FIG. 4 and described more fully below. By swiveling the two arms 440, 450, an operator can position the flat panel display device 430 beyond the perimeter of the ultrasound system cart 410.

While FIG. 4 shows two swiveling arms 440, 450, there are many other designs for the support apparatus, which allow the flat panel display device 430 to be tilted, swiveled, adjusted for height, and extended horizontally. When these designs are used in combination, the flat panel display device can be tilted greater than 90 degrees from a vertical axis, be swiveled by more than 90 degrees, have a height adjustment greater than about 6 inches, and have a horizontal extension beyond the confines of the ultrasound system cart greater than about 6 inches.

It is important to note that the alternative designs described below are merely examples. Other alternatives, though not illustrated, can be used to provide the flat panel display device with a wide range of motion.

FIG. 5 illustrates two hinges 540, 550 attached to a first arm 560. The first hinge 540 connect the first arm 560 to the flat panel display device 530, allowing the display device 530 to tilt. The second hinge 550 connects the first arm 560 to a second arm 570, providing the display device 530 with vertical extension. The second arm 570 attaches to the cart 510 with a device 580 that allows the display device 530 to swivel. The arms 560, 570 cooperate to allow the display device 530 to extend beyond the footprint of the cart 510.

Figure 6:
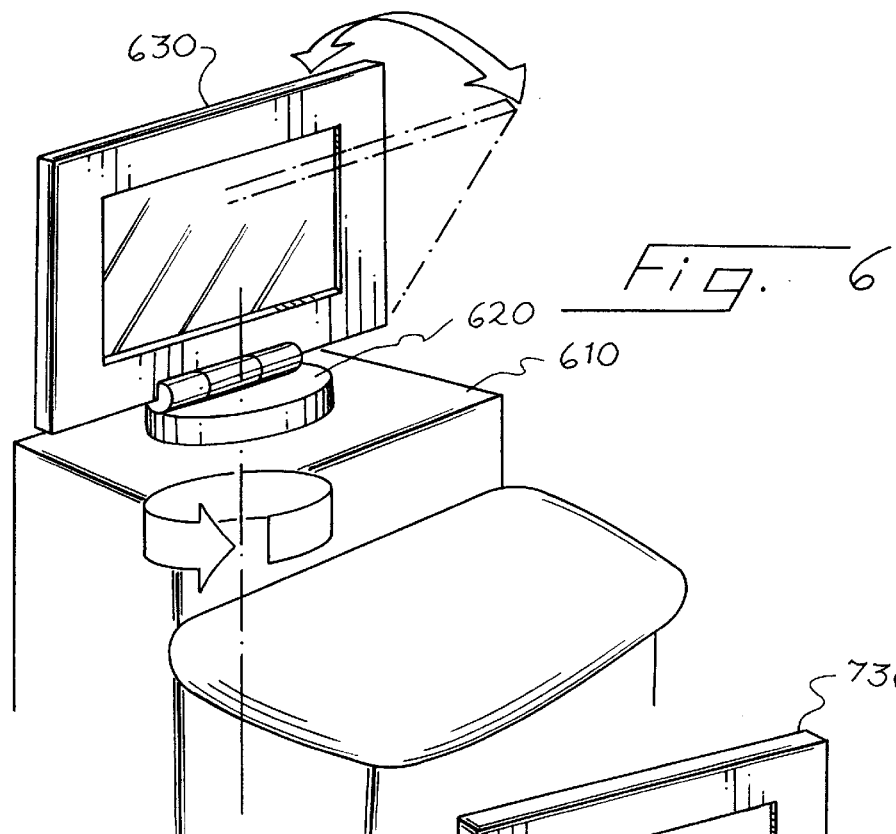
FIG. 6 is a perspective view of a means for positioning a flat panel display device using a swiveling hinge to tilt and swivel the display device.

In FIG. 6, a swiveling hinge 620 connects the display device 630 to the cart 610. By articulating this hinge 620, the operator can tilt and swivel the display device 630.

Figure 7:
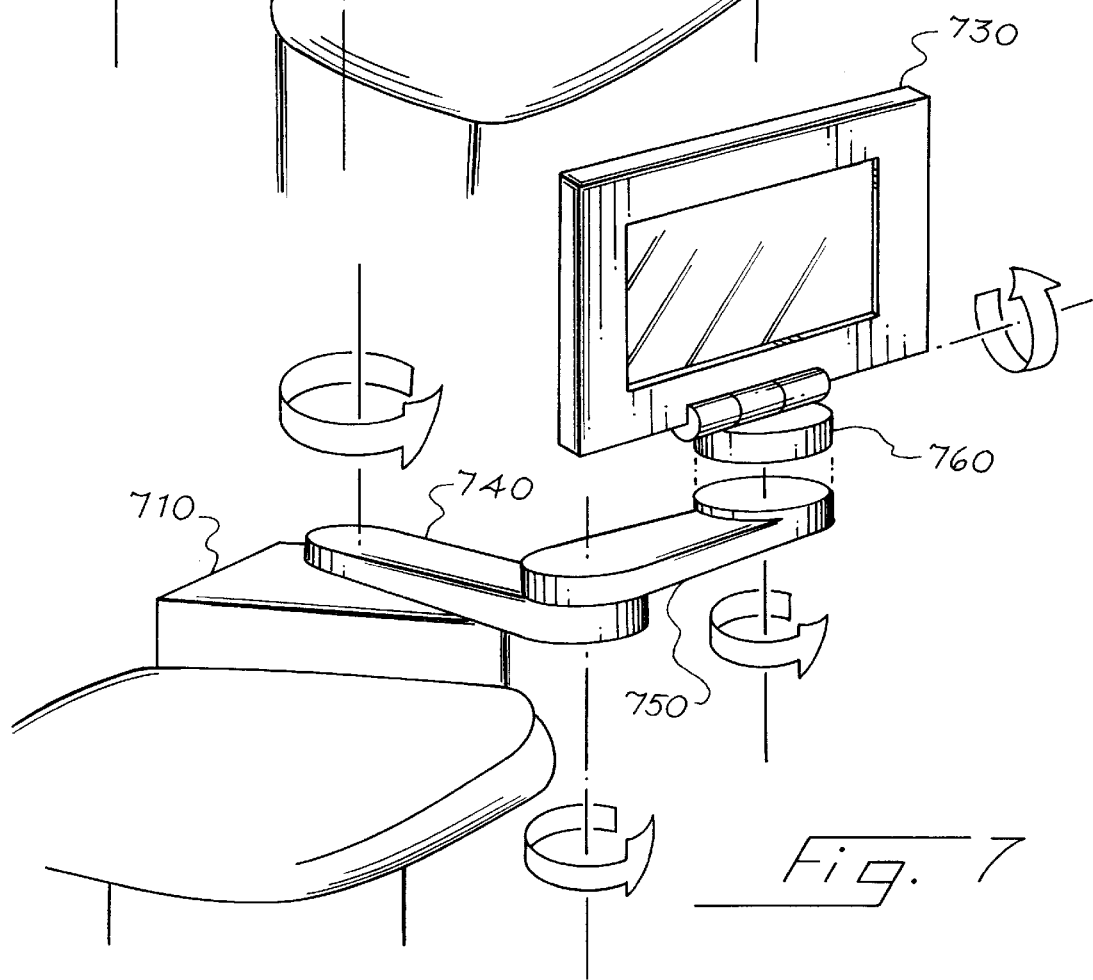
FIG. 7 is a perspective view of a means for positioning a flat panel display device using a swiveling arm to horizontally extend, swivel, and tilt the display device.

The flat panel display device 730 shown in FIG. 7 is attached to the ultrasound system cart 710 by two swiveling arms 740, 750. With these arms 740, 750, the operator can horizontally position the display device 730 outside the perimeter of the cart 710. One swiveling arm 750 connects to the display device 730 with a swiveling hinge 760. With this connection, the operator can swivel and tilt the display device 730 to a desired position.

The display device 830 shown in FIG. 8 is connected to the cart 810 with a ball and socket joint 820 which provides the display device 830 with three axes of rotation. An operator can articulate a swiveling yoke 920 to tilt and swivel the display device 930 shown in FIG. 9 and to adjust the fore-and-aft position of the display device 930.

Figure 10:
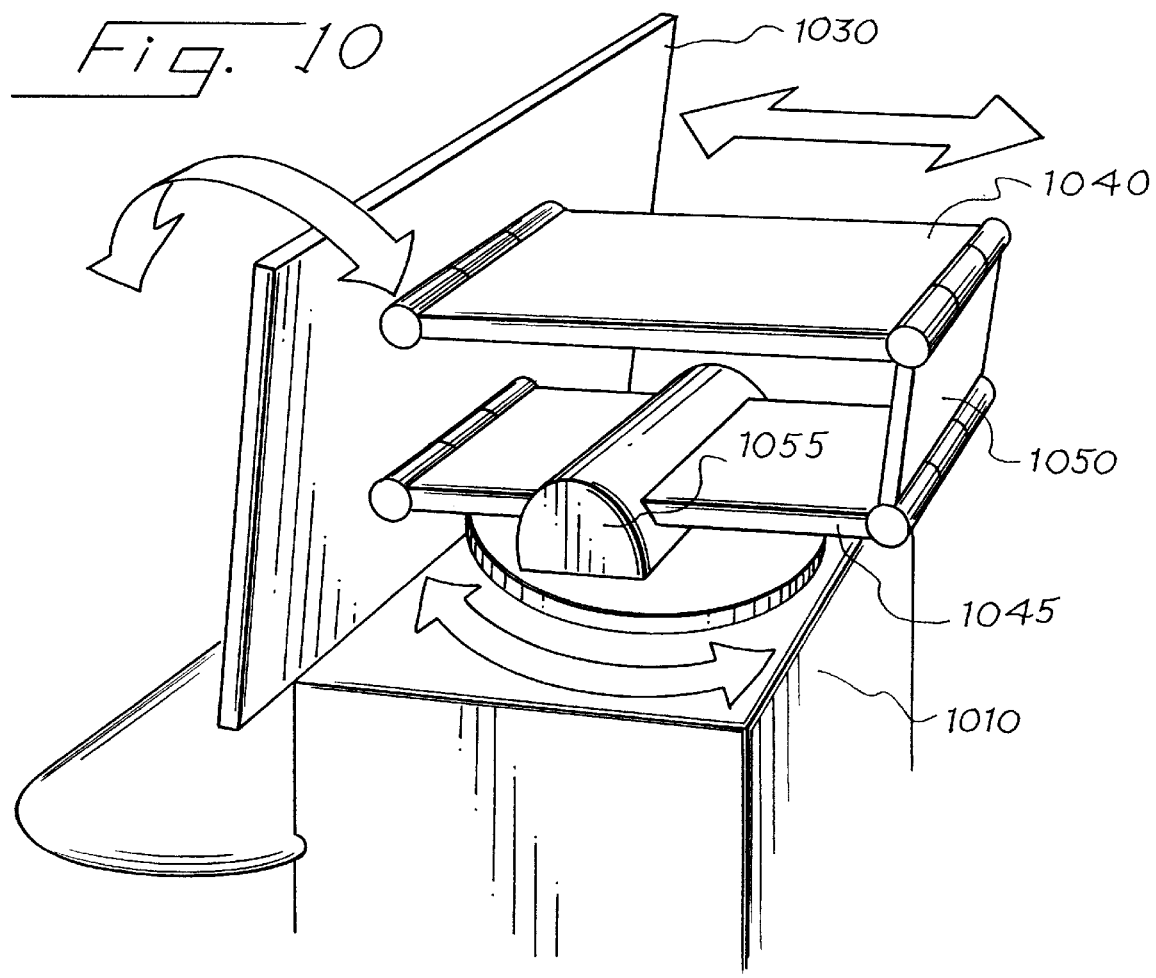
FIG. 10 is a perspective view of a means for positioning a flat panel display device using a bar-linkage to tilt, swivel, and adjust a fore-and-aft position of the display device.
Figures 10A, 10B:
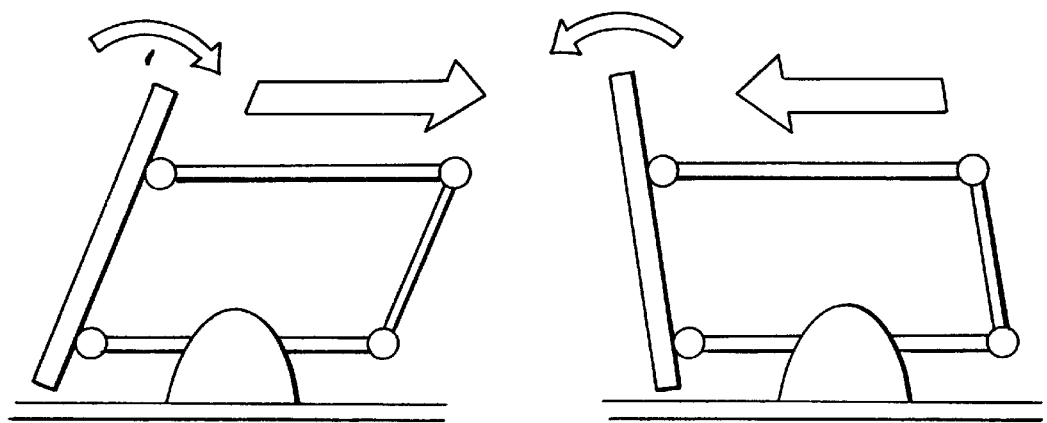
FIG. 10A is a side view of the means shown in FIG. 10, illustrating the display in a first position.
FIG. 10B is another side view of the means shown in FIG. 10, illustrating the display in a second position.

FIG. 10 illustrates the movements possible when a bar-linkage device connects the display device 1030 to the cart 1010. The bar-linkage device comprises an upper bar 1040 and a lower bar 1045. One end of each bar 1040, 1045 is hinged to the display device 1030, and other end of each bar is hinged to a connected bar 1050. The lower bar 1045 is slideable through a swiveling disc 1055, thereby connecting the display device 1030 to the cart 1010. Articulation of the bar-linkage device allows the operator to tilt, swivel, and adjust the fore and aft position of the display device 1030, as shown in FIGS. 10A and 10B.

In the embodiment of FIG. 11, a hinge 1125 connects the display device 1130 to a telescopic slide 1120, which connects to the cart 1110. With the hinge 1125 and telescopic slide 1120, the operator can tilt and adjust the vertical position of the display device 1130.

A similar positioning scheme is illustrated in the embodiment of FIGS. 12 and 12A, in which a hinge 1225 connects the display device 1230 to a sleeve 1215, which can be positioned along a vertical slide 1220 to adjust the vertical position of the display device 1230. Additionally, the display device 1230 can be tiled away from the slide 1220 through articulation of the hinge 1225.

Figure 13:
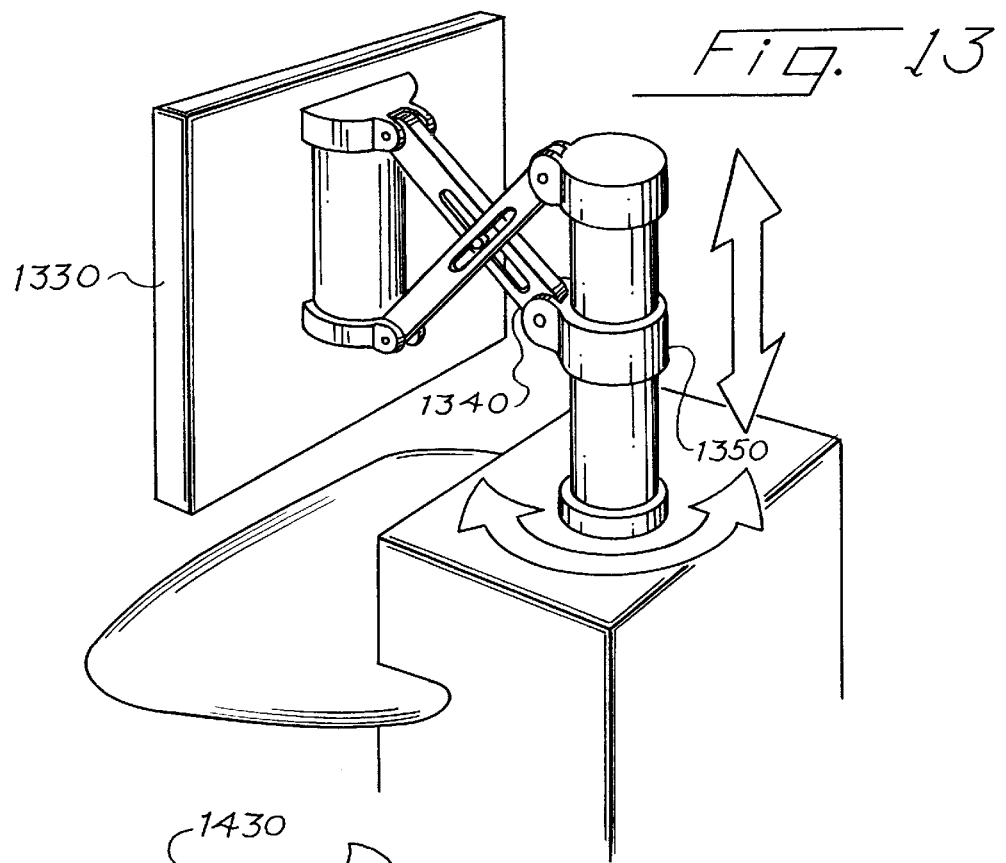
FIG. 13 is a perspective view of a means for positioning a flat panel display device using a bar-linkage device for tilting the display device and a circular-slide device for swiveling the display device and adjusting its vertical position.

FIG. 13 illustrates an embodiment which includes a bar-linkage device 1340 for tilting the display device 1330 and a circular-slide device 1350 for swiveling the display device 1330 and adjusting its vertical position.

It is important to note that the above-described positioning means are merely examples, and many other arrangements are possible, including any desired combination of the linkages and joints described above.

Advantages

In an optimal examination environment, the operator can separately position the ultrasound generator and the display device to accommodate ultrasound system size, patient positioning, and physical layout of the examination room.

The CRT display device cannot be positioned away from the ultrasound system cart and closer to the patient because of the CRT display's size and weight. If the CRT display were positioned away from the cart, such as with a mechanical arm, the cart would become unstable.

The embodiments described above provide great flexibility in positioning the display device relative to the cart. With this flexibility, the operator can position the display device away from the cart and closer to the patient, moving the display device into his line of sight during the examination. This generally increases operator efficiency and specifically improves system ergonomics by reducing operator fatigue and body strain.

THIRD PREFERRED EMBODIMENT

Figure 14:
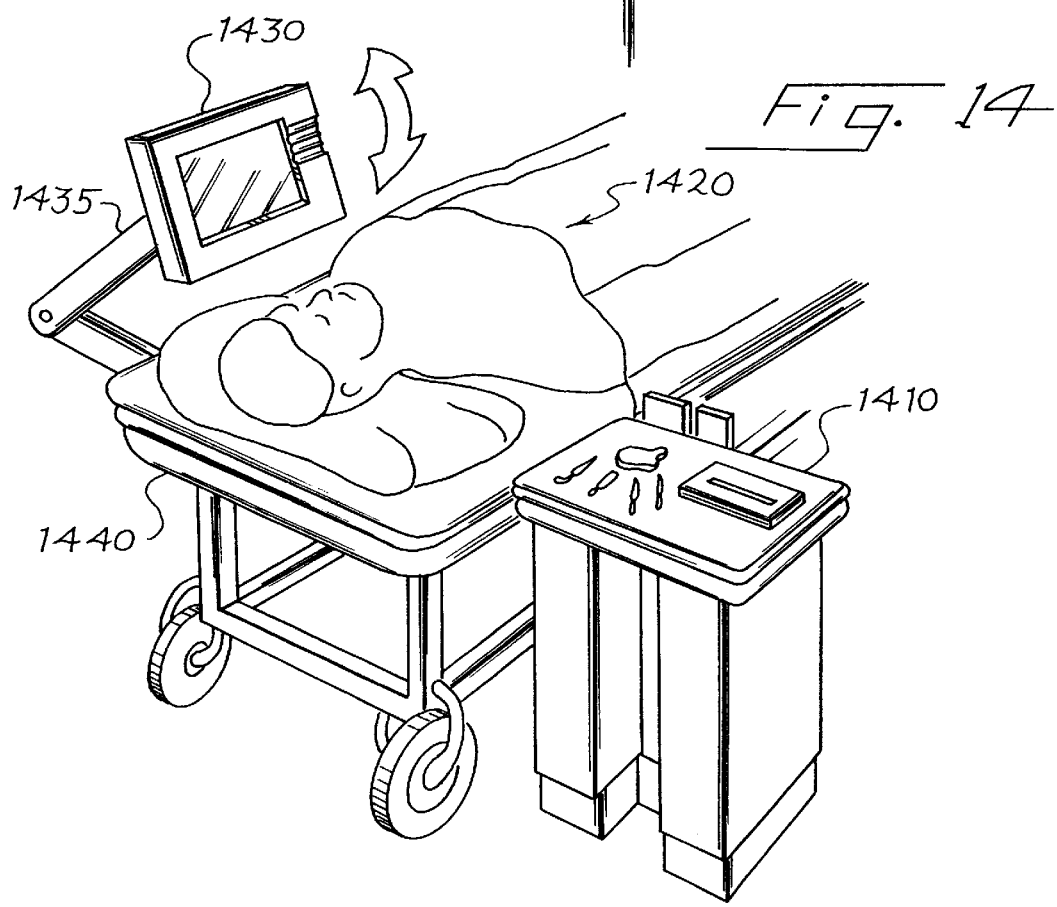
FIG. 14 is a perspective view of a third preferred embodiment in which a flat panel display device comprises a means for positioning the display device with respect to a patient. The flat panel display device is secured to a structure physically independent of an ultrasound system generator.

FIG. 14 shows a patient 1420, a bed 1440, a flat panel display device 1430 attached to the bed 1440 by a support apparatus 1435, and a structure 1410 housing an ultrasound image generator. Instead of being supported by the ultrasound system cart (as described in the above embodiments), the flat panel display device 1430 attaches to a support apparatus 1435 that is not physically connected to the structure 1410 housing the ultrasound image generator. For example, as shown in FIG. 14, the display device 1430 attaches to a support apparatus 1435 attached to a patient's bed 1440.

Figure 15:
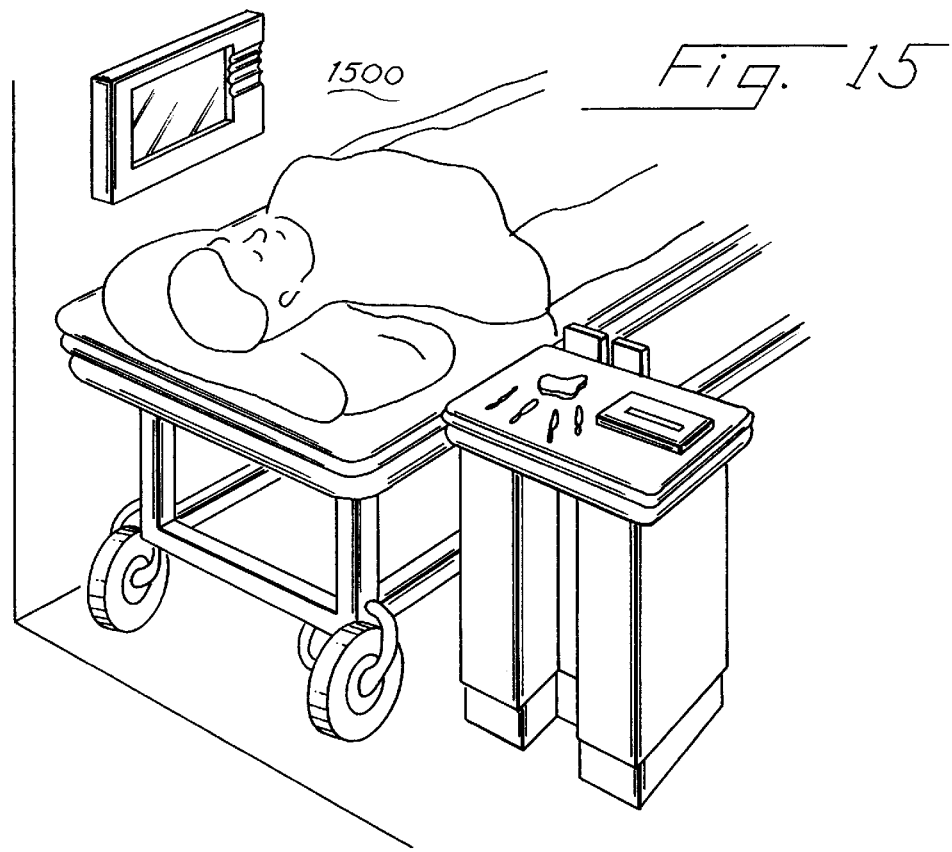
FIG. 15 is a perspective view of the third preferred embodiment in which the flat panel display device attaches to a wall behind a patient.
Figure 16:
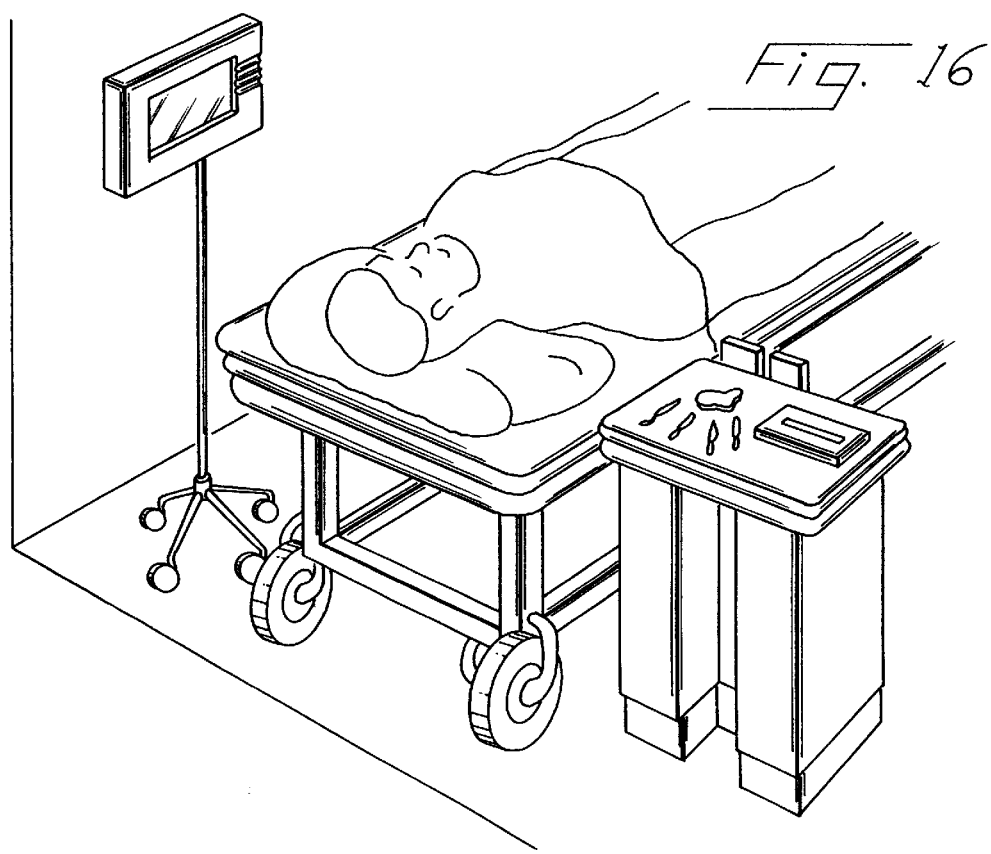
FIG. 16 is a perspective view of the third preferred embodiment in which the flat panel display device attaches independently to a floor.

Because the display 1430 is small and lightweight, a wide variety of structures can be adapted to support the display device 1430. For example, the display device can be supported by a gurney, attached to a wall 1500 (see FIG. 15) behind the patient, suspended from the ceiling over the patient's bed, or attached independently to the floor (as shown in FIG. 16). Of course, many other structures beyond those listed can be used to support the display device.

Additionally, any of the positioning means described in the second preferred embodiment may be used in this preferred embodiment to position the display device anywhere with respect to the patient.

Advantages

The third preferred embodiment provides the operator with additional advantages. By not being secured to a cart, the display device 1430 has a default position closer to the patient 1420. This may allow for less maneuvering of the display device 1430 to position it in the operator's line of sight. Because the display device 1430 is much lighter than a CRT display, there is less danger in positioning the display near or over the patient 1420. Additionally, this embodiment allows for positioning of the display device when there is no cart (e.g., when the ultrasound system generator is stationary and located farther away from the patient).

It is intended that the foregoing detailed description be understood as an illustration of selected forms that the invention can take and not as a definition of the invention. It is only the following claims, including all equivalents, which are intended to define the scope of this invention.

What is claimed is:

1. A diagnostic medical imaging ultrasound system comprising:

an ultrasound system cart;

an ultrasound image generator integrated with the cart, the image generator comprising a transmit beamformer, a receive beamformer, and a signal processor responsive to the receive beamformer; and a flat panel display device supported by the cart and responsive to the signal processor, the flat panel display device being operative to display an ultrasound image generated by the ultrasound image generator.

2. The invention of claim 1, wherein the ultrasound system is characterized by a center of gravity less than about 24 inches from a floor.

3. The invention of claim 1, wherein the ultrasound system cart is characterized by a front and rear wheel centerline, and wherein the ultrasound system is characterized by a center of gravity less than about 14 inches from the front and rear wheel centerlines.

4. The invention of claim 1, wherein the ultrasound system cart is characterized by a wheelbase length, and wherein the ultrasound system cart is characterized by a wheelbase length less than about 27 inches.

5. The invention of claim 1, wherein the ultrasound system cart is characterized by a track width, and wherein the ultrasound system cart is further characterized by a track width less than about 22 inches.

6. The invention of claim 1, further comprising means for adjustably positioning the flat panel display device with respect to the cart.

7. A diagnostic medical imaging ultrasound system for forming an ultrasound image of a patient, the system comprising:

an ultrasound cart, an ultrasound image generator, the image generator comprising a transmit beamformer, a receive beamformer, and a signal processor responsive to the receive beamformer, said ultrasound image generator being integrated with said ultrasound system cart, a flat panel display device responsive to the signal processor, the flat panel display device being operative to display an ultrasound image generated by the ultrasound image generator; and a support apparatus attaching the flat panel display device to a structure physically independent of the ultrasound system cart, the support apparatus comprising means for positioning the flat panel display device with respect to a patient.

8. The invention of claim 7, wherein the support apparatus is adapted to attach the flat panel display device to a bed.

9. The invention of claim 7, wherein the support apparatus is adapted to attach the flat panel display device to a wall.

10. The invention of claim 7, wherein the support apparatus is adapted to attach the flat panel display device independently to a floor.

11. The invention of claim 1 or 7, wherein the flat panel display device is adapted to produce an image having a contrast ratio exceeding about 300:1.

12. The invention of claim 1 or 7, the flat panel display device is adapted to produce an image having a response time of less than about 33 milliseconds.

13. The invention of claim 1 or 7, wherein the flat panel display device comprises a face, and is adapted to produce an image characterized by an angular fidelity of the properties of the rendered light with a ±45 degree cone originating from and comprising an axis of symmetry upright to the face of the flat panel display.

14. The invention of claim 1 or 7, wherein the flat panel display device is adapted to provide an active image area larger than about 10 inches diagonal and a total number of color pixels greater than about 400,000.

15. The invention of claim 6 or 7, wherein the means for positioning comprises means for tilting the flat panel display device over a range greater than 90 degrees.

16. The invention of claim 6 or 7, wherein the means for positioning comprises means for swiveling the flat panel display device through a range greater than 90 degrees.

17. The invention of claim 6 or 7, wherein the flat panel display device is characterized by a horizontal position, and wherein the means for positioning comprises means for extending the horizontal position through a range greater than about 6 inches.

18. The invention of claim 6 or 7, wherein the ultrasound image generator comprises a perimeter, and wherein the means for positioning comprises means for extending the flat panel display device beyond the perimeter of the ultrasound image generator.

19. The invention of claim 6 or 7, wherein the flat panel display device is characterized by a height, and wherein the means for positioning comprises means for adjusting the height of the flat panel display device.

20. The invention of claim 6 or 7, wherein the means for positioning comprises:
   at least one arm having a first end and a second end, the first end attaching to the flat panel display device; and
   at least one hinge attaching to the second end for horizontally and vertically extending the flat panel display device.

21. The invention of claim 6 or 7, wherein the means for positioning comprises a swiveling hinge, articulation of the swiveling hinge tilting the flat panel display device about a horizontal axis and swiveling the flat panel display device about a vertical axis.

22. The invention of claim 6 or 7, wherein the means for positioning comprises a pivoting arm for horizontally extending the flat panel display device.

23. The invention of claim 6 or 7, wherein the means for positioning comprises a ball and socket, articulation of the ball and socket providing the flat panel display device with three axes of rotation.

24. The invention of claim 6 or 7, wherein the means for positioning comprises a swiveling yoke, articulation of the yoke tilting the flat panel display device about a horizontal axis, swiveling the flat panel display device about a vertical axis, and vertically and horizontally extending the flat panel display device.

25. The invention of claim 6 or 7, wherein the means for positioning comprises a swiveling bar-linkage device for tilting the flat panel display device about a horizontal axis, swiveling the flat panel display device about a vertical axis, and horizontally extending the flat panel display device.

26. The invention of claim 6 or 7, wherein the means for positioning comprises a telescopic slide for vertically extending the flat panel display device.

27. The invention of claim 6 or 7, wherein the means for positioning comprises:
   a tongue; and
   a sleeve attaching to the flat panel display device and slidable along the tongue to provide the flat panel display device with vertical extension along the tongue.

28. The invention of claim 6 or 7, wherein the means for positioning comprises a bar-linkage device for tilting the flat panel display device about a horizontal axis.

29. The invention of claim 6 or 7, wherein the means for positioning comprises a circular slide for vertically extending the flat panel display device.

* * * * *

UNITED STATES PATENT AND TRADEMARK OFFICE
CERTIFICATE OF CORRECTION

PATENT NO. : 5,924,988
DATED : July 20, 1999
INVENTOR(S) : Burris et al.

It is certified that error appears in the above-identified patent and that said Letters Patent is hereby corrected as shown below:

In column 4, line 13, please change "is" (second occurrence) to --in--.

In column 6, line 60, please change "tiled" to --tilted--

In claim 7, line 4, before "cart" please insert --system--; and on line 8, please change "said" to --the--.

In claim 12, line 1, after "7," please insert --wherein--.

Signed and Sealed this

Twenty-sixth Day of December, 2000

Q. TODD DICKINSON

*Attest:*

*Attesting Officer*          *Director of Patents and Trademarks*